(12) United States Patent
Jeong et al.

(10) Patent No.: US 11,338,136 B2
(45) Date of Patent: May 24, 2022

(54) CRANIAL NERVE CONTROL DEVICE USING BOTH OF MONITORING ACCORDING TO REAL-TIME BRAIN ACTIVITY CHANGE AND COMBINED CENTRAL AND PERIPHERAL NERVE STIMULATION

(71) Applicant: CYBERMEDIC CO., LTD., Iksan-si (KR)

(72) Inventors: Ho Choon Jeong, Gunsan-si (KR); Hyun Hee Lee, Jeonju-si (KR); Sang Sea Lee, Jeonju-si (KR); Myoung Choon Kim, Iksan-si (KR)

(73) Assignee: CYBERMEDIC CO., LTD., Iksan-si (KR)

( * ) Notice: Subject to any disclaimer, the term of this patent is extended or adjusted under 35 U.S.C. 154(b) by 56 days.

(21) Appl. No.: 16/757,428

(22) PCT Filed: Nov. 1, 2018

(86) PCT No.: PCT/KR2018/013168
§ 371 (c)(1),
(2) Date: Apr. 20, 2020

(87) PCT Pub. No.: WO2019/107768
PCT Pub. Date: Jun. 6, 2019

(65) Prior Publication Data
US 2021/0023369 A1    Jan. 28, 2021

(30) Foreign Application Priority Data
Nov. 30, 2017   (KR) ........................ 10-2017-0163581

(51) Int. Cl.
*A61N 1/04*     (2006.01)
*A61N 1/20*     (2006.01)
*A61N 1/36*     (2006.01)

(52) U.S. Cl.
CPC ....... *A61N 1/36025* (2013.01); *A61N 1/0456* (2013.01); *A61N 1/0484* (2013.01); *A61N 1/20* (2013.01); *A61N 1/36031* (2017.08)

(58) Field of Classification Search
CPC ............ A61N 1/36025; A61N 1/36031; A61N 1/0456; A61N 1/0484; A61N 1/20;
(Continued)

(56) References Cited

U.S. PATENT DOCUMENTS 7,756,584 B2 *   7/2010   Sheffield ............ A61N 1/36025
                                                              607/45
2011/0224753 A1   9/2011   Palermo et al.
(Continued)

FOREIGN PATENT DOCUMENTS

JP     2010-519003 A    6/2010
JP     2016-511651 A    4/2016
(Continued)

OTHER PUBLICATIONS

International Search Report for PCT/KR2018/013168 dated Mar. 8, 2019 from Korean Intellectual Property Office.

*Primary Examiner* — Carl H Layno
*Assistant Examiner* — Anh-Khoa N Dinh
(74) *Attorney, Agent, or Firm* — Revolution IP, PLLC (57) ABSTRACT

A cranial nerve control device includes: goggles worn on a patient head; a functional electric stimulator adapted to apply peripheral nerve stimulation to a patient; a plurality of module guides provided to the goggles; a functional electric stimulator controller adapted to control the functional electric stimulator; a transcranial current stimulator-combined near-infrared spectroscopy measurement module controller adapted to control the transcranial current stimulator-combined functional near-infrared spectroscopy measurement module; and a simulation device connected to both the
(Continued)

transcranial current stimulator-combined near-infrared spectroscopy measurement module controller and the functional electric stimulator to provide feedback of a transcranial current stimulation control signal to the transcranial current stimulator and feedback of a functional electrical stimulation control signal to the functional electric stimulator while monitoring the patient brain activity.

3 Claims, 9 Drawing Sheets

(58) Field of Classification Search
CPC .... A61N 1/0492; A61N 1/36003; A61B 5/00; A61B 5/0075; A61B 5/24; A61B 5/316; A61B 5/369

See application file for complete search history.

(56) References Cited

U.S. PATENT DOCUMENTS

| | | |
|---|---|---|
| 2011/0245708 A1 | 10/2011 | Finkel et al. |
| 2013/0204315 A1* | 8/2013 | Wongsarnpigoon ... A61N 1/361 607/45 |
| 2014/0288614 A1* | 9/2014 | Hagedorn ............ A61B 5/0006 607/45 |
| 2015/0321000 A1 | 11/2015 | Rosenbluth et al. |
| 2017/0340260 A1 | 11/2017 | Chowdhury et al. |

FOREIGN PATENT DOCUMENTS

| | | | |
|---|---|---|---|
| KR | 10-2014-0052781 A | 5/2014 | |
| KR | 10-2017-0128232 A | 11/2017 | |
| WO | WO-2016182947 A1 * | 11/2016 | ........... A61N 1/0456 |

* cited by examiner

CRANIAL NERVE CONTROL DEVICE USING BOTH OF MONITORING ACCORDING TO REAL-TIME BRAIN ACTIVITY CHANGE AND COMBINED CENTRAL AND PERIPHERAL NERVE STIMULATION

TECHNICAL FIELD

The present invention relates to a cranial nerve control device adapted to monitor a combined stimulation device, in which a transcranial current stimulation{tCS=tACS (Transcranial Alternate Current Stimulation)+tDCS (Transcranial Direct Current Stimulation)} device for central nerve stimulation is combined with a functional electrical stimulation (FES) device for peripheral nerve stimulation, and a brain activity simultaneous measurement module of functional near-infrared spectroscopy (fNIRS) for real-time brain activity monitoring, based on monitoring according to real-time brain activity change and combined central and peripheral nerve stimulation.

BACKGROUND ART

Figure 1:
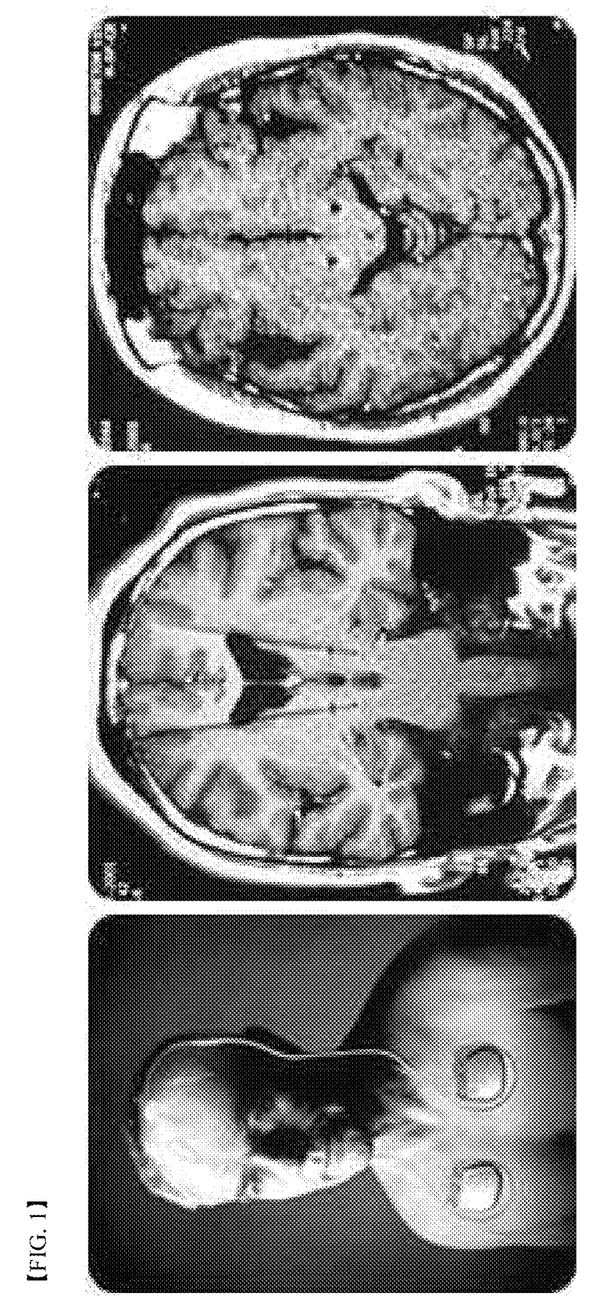
FIG. 1 and FIG. 2 are pictures illustrating a conventional invasive deep brain stimulation method in which electrodes are inserted into the brain to stimulate the brain.
Figure 2:
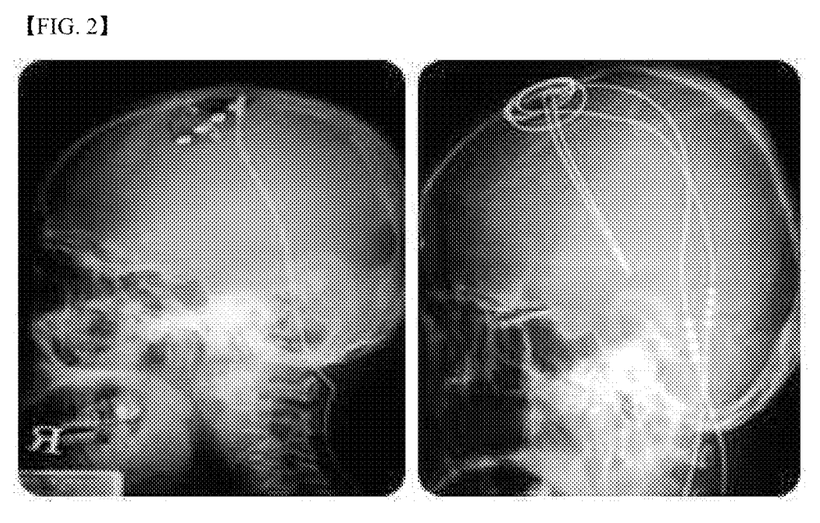
Figure 3:
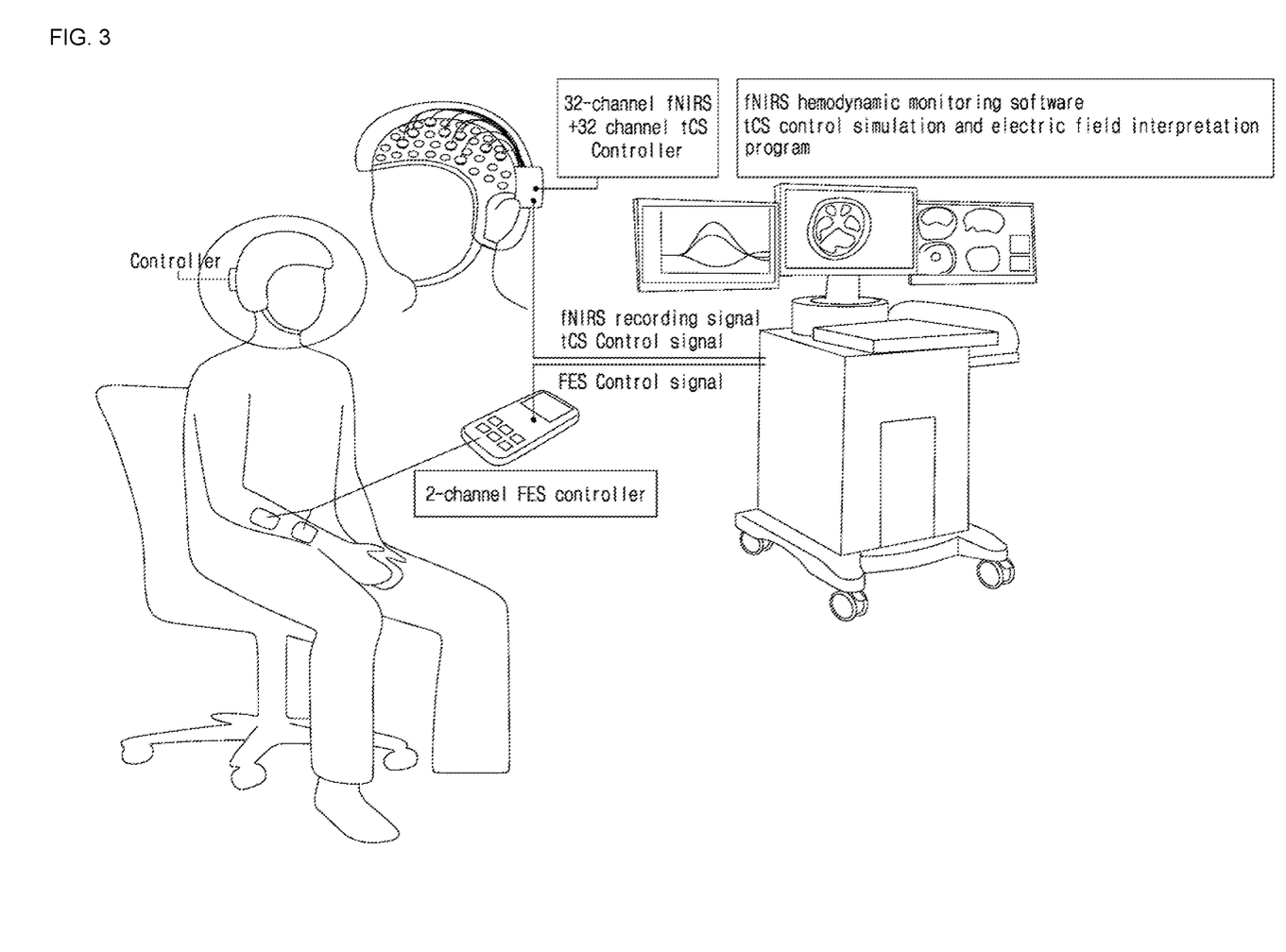
FIG. 3 is a diagram of a cranial nerve control device based on monitoring according to real-time brain activity change and combined central and peripheral nerve stimulation according to the present invention.
Figure 4:
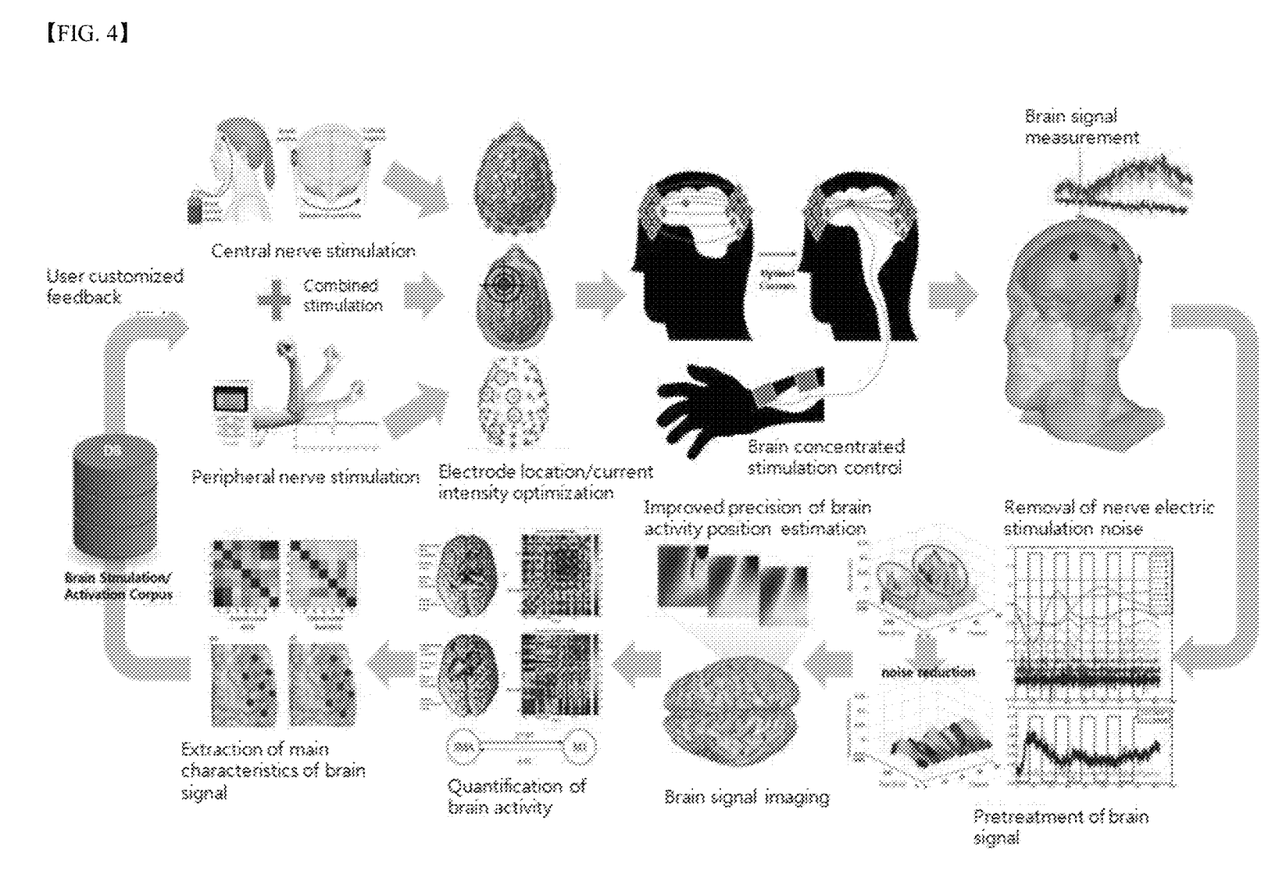
FIG. 4 is a block diagram of the cranial nerve control device based on monitoring according to real-time brain activity change and combined central and peripheral nerve stimulation according to the present invention.
Figure 5:
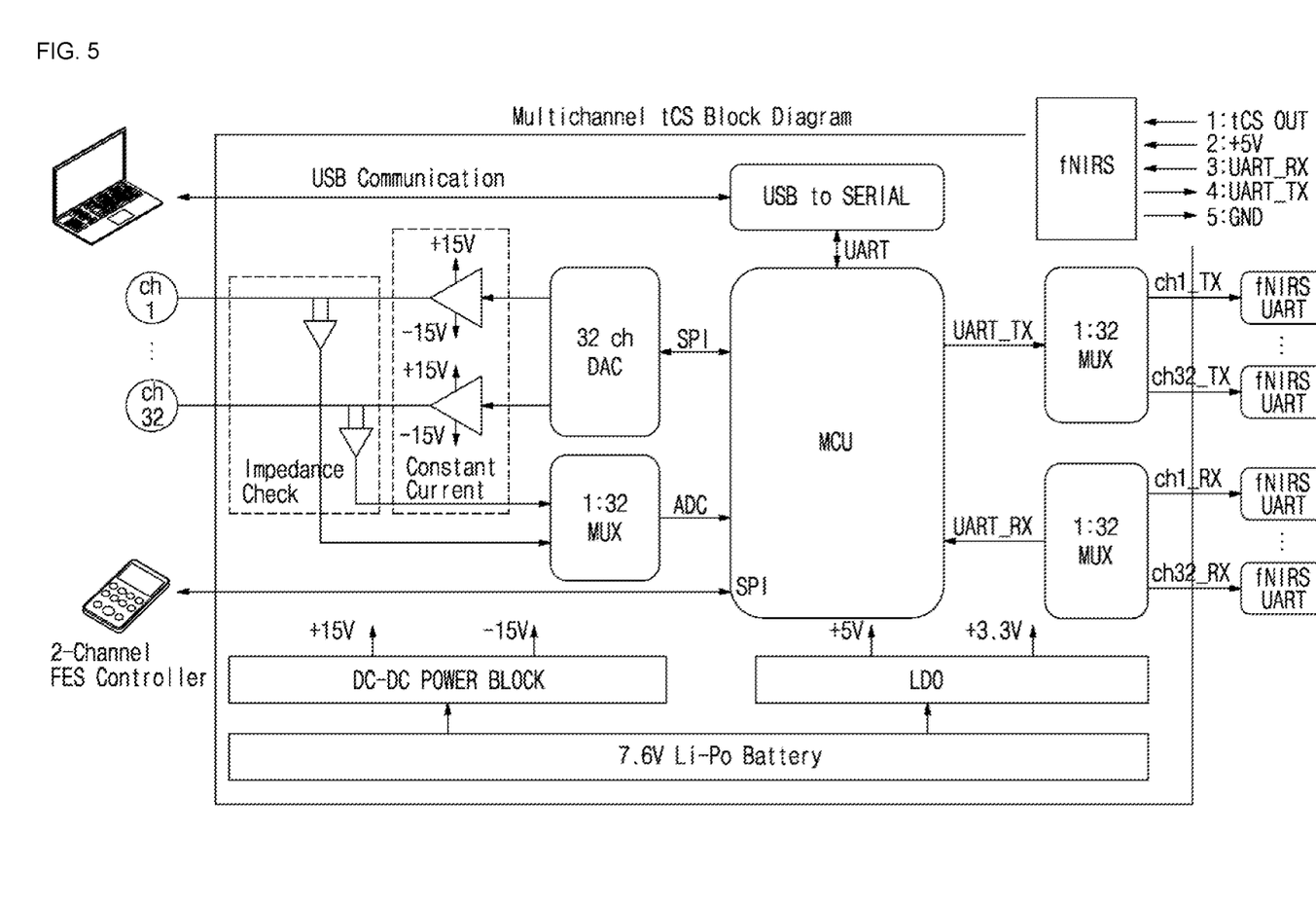
FIG. 5 is a block diagram of a module device for measurement of brain activity for multi-channel transcranial current stimulation and coupling of a 2 channel FES stimulator according to the present invention.
Figure 6:
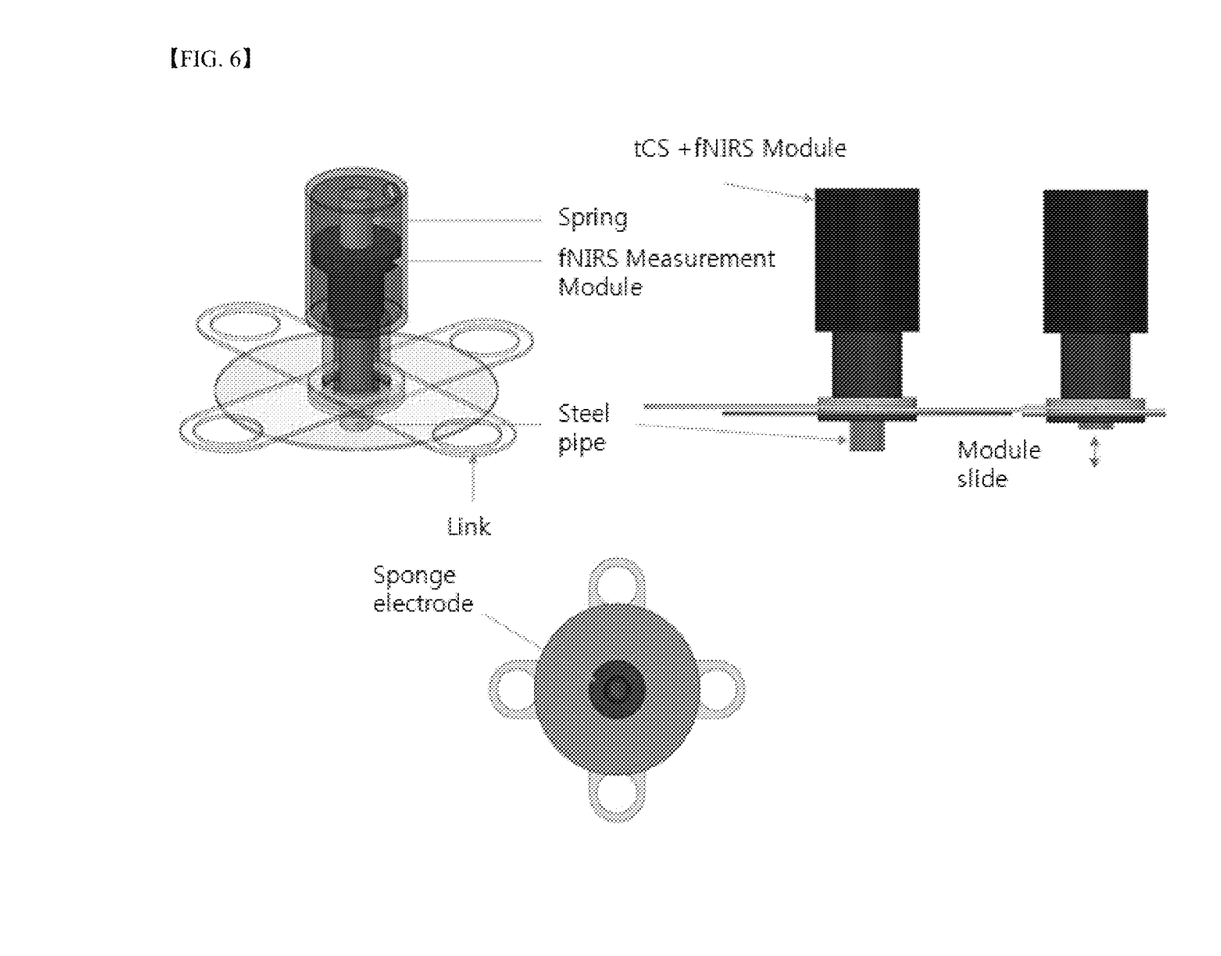
FIG. 6 is a block diagram illustrating hardware, interface and software treatment processes for real-time control of the cranial nerve control device based on monitoring according to real-time brain activity change and combined central and peripheral nerve stimulation according to the present invention.

As shown in FIG. 1 and FIG. 2, although invasive deep brain stimulation performed by stimulating the brain through electrodes inserted into the brain is used as treatment for hydrocephalus, Parkinson's disease, dystonia, and the like, side effects, such as surgical side effects and unintended seizure attacks, have been reported. Despite an excellent treatment effect on certain serious diseases, this method has a problem of difficulty in application to treatment of many diseases due to a risk in actual application to surgery and complicated operation.

DISCLOSURE

Technical Problem

The present invention has been conceived to solve the problem of the background art and it is one aspect of the present invention to provide a cranial nerve control device based on monitoring according to real-time brain activity change and combined central and peripheral nerve stimulation, which can provide convenience for enriched human life while enabling dramatic treatment of brain diseases, as a technology for automatically understanding functional activation of the user brain through real-time detection of structurally and functionally complex brain cognition information and performing functional electrical stimulation of the brain.

It is another aspect of the present invention to provide a cranial nerve control device adapted to automatically control electrical stimulation through understanding of an activated state of the brain without targeting a damaged brain region of a person, based on monitoring according to real-time brain activity change and combined central and peripheral nerve stimulation, as a technology based on artificial intelligence-based feedback of brain signals and brain electrical stimulation.

Technical Solution

In accordance with a first embodiment of the present invention, a cranial nerve control device based on monitoring according to real-time brain activity change and combined central and peripheral nerve stimulation includes: goggles worn on a patient head to measure patient brain activity; a module guide fastened to each of a plurality of punched portions arranged at the same intervals on the goggles; a 32-channel fNIRS+32-channel tCS controller connected to each of modules of the module guide to control the modules; a 2-channel FES controller connected to two peripheral nerve stimulators worn on a patient wrist to control the peripheral nerve stimulators; and a simulation device connected to both the 32-channel fNIRS+32-channel tCS controller and the 2-channel FES controller and monitoring both the 32-channel fNIRS+32-channel tCS controller and the 2-channel FES controller in response to a brain activity measurement signal by functional near-infrared spectroscopy (fNIRS), a transcranial current stimulation (tCS) control signal and a functional electrical stimulation (FES) control signal.

Functional near-infrared spectroscopy (fNIRS)-based hemodynamic monitoring software and a transcranial current stimulation (tCS) interpretation program may be installed in the simulation device. The module guide may include: a module guide securing hole (①) formed in each of the punched portions of the goggles and having a cylindrical shape open at upper and lower sides thereof; a module case (④) inserted into the module guide securing hole (①) and having a cylindrical shape open at a lower side thereof and closed at an upper side thereof; a tCS+fNIRS module (⑤) disposed to move upwards or downwards in the module case (④) and having a lower end brought into contact with the scalp and composed of a piston-shaped steel pipe; and a spring (⑨) pushing an upper surface of the tCS+fNIRS module (⑤) in a downward direction in the module case (④).

Advantageous Effects

According to the present invention, the cranial nerve control device based on monitoring according to real-time brain activity change and combined central and peripheral nerve stimulation can automatically control electrical stimulation through understanding of an activated state of the brain without targeting a damaged brain region, thereby providing convenience for enriched human life while enabling dramatic treatment of brain diseases, as a technology for automatically understanding functional activation of a user brain through real-time detection of structurally and functionally complex brain cognition based on artificial intelligence-based feedback of brain signals and brain electrical stimulation.

BEST MODE

In accordance with a first embodiment of the present invention, a cranial nerve control device based on monitoring according to real-time brain activity change and combined central and peripheral nerve stimulation includes: goggles worn on a patient head to measure patient brain activity; a module guide fastened to each of a plurality of punched portions arranged at the same intervals on the goggles; a 32-channel fNIRS+32-channel tCS controller connected to each of modules of the module guide to control the modules; a 2-channel FES controller connected to two peripheral nerve stimulators worn on a patient wrist to control the peripheral nerve stimulators; and a simulation device connected to both the 32-channel fNIRS+32-channel tCS controller and the 2-channel FES controller and monitoring both the 32-channel fNIRS+32-channel tCS controller and the 2-channel FES controller in response to a brain activity measurement signal by functional near-infrared spectroscopy (fNIRS), a transcranial current stimulation (tCS) control signal and a functional electrical stimulation (FES) control signal.

Mode for Invention

Hereinafter, exemplary embodiments of the present invention will be described in detail with reference to the accompanying drawings such that the present invention can be easily implemented by those skilled in the art. Like components will be denoted by like reference numerals throughout the drawings. In addition, description of known functions and constructions which can unnecessarily obscure the subject matter of the present invention will be omitted. Further, it should be noted that the drawings are not to precise scale and some of the dimensions, such as width, length, thickness, and the like, are exaggerated, minimized or simplified for clarity of description in the drawings. However, these features can be easily understood by those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and "has," when used in this specification, specify the presence of stated features, steps, operations, elements, and/or components, but do not preclude the presence or addition of one or more other features, steps, operations, elements, components, and/or groups.

Unless otherwise defined herein, all terms including technical or scientific terms used herein have the same meanings as commonly understood by those skilled in the art to which the present invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

Hereinafter, exemplary embodiments of the present invention will be described in detail with reference to the accompanying drawings. Description of known functions and constructions which can unnecessarily obscure the subject matter of the present invention will be omitted.

EXAMPLE

A cranial nerve control device based on monitoring according to real-time brain activity change and combined central and peripheral nerve stimulation according to the present invention will be described with reference to FIGS. 3 to 9.

Combined central and peripheral nerve stimulation refers to transcranial current stimulation {tCS=tACS (Transcranial alternate Current Stimulation)+tDCS (Transcranial Direct Current Stimulation)} and functional electrical stimulation (FES: functional electrical stimulation) for peripheral nerve stimulation.

Herein, real-time brain activity monitoring refers to a brain activity simultaneous measurement module device of functional near-infrared spectroscopy (functional near-infrared spectroscopy; fNIRS).

The combined central and peripheral nerve stimulation and the real-time brain activity monitoring are collectively referred to as the cranial nerve control device.

According to the present invention, the cranial nerve control device based on monitoring according to real-time brain activity change and combined central and peripheral nerve stimulation includes: goggles worn on a patient head to measure patient's brain activity; a module guide fastened to each of a plurality of punched portions arranged at the same intervals on the goggles; a 32-channel fNIRS+32-channel tCS controller connected to each of modules of the module guide to control the modules; a 2-channel FES controller connected to two peripheral nerve stimulators worn on a patient wrist to control the peripheral nerve stimulators; and a simulation device connected to both the 32-channel fNIRS+32-channel tCS controller and the 2-channel FES controller and monitoring both the 32-channel fNIRS+32-channel tCS controller and the 2-channel FES controller in response to a brain activity measurement signal by functional near-infrared spectroscopy (fNIRS), a transcranial current stimulation (tCS) control signal and a functional electrical stimulation (FES) control signal.

Functional near-infrared spectroscopy (fNIRS)-based hemodynamic monitoring software and a transcranial current stimulation (tCS) interpretation program are installed in the simulation device.

Figure 7:
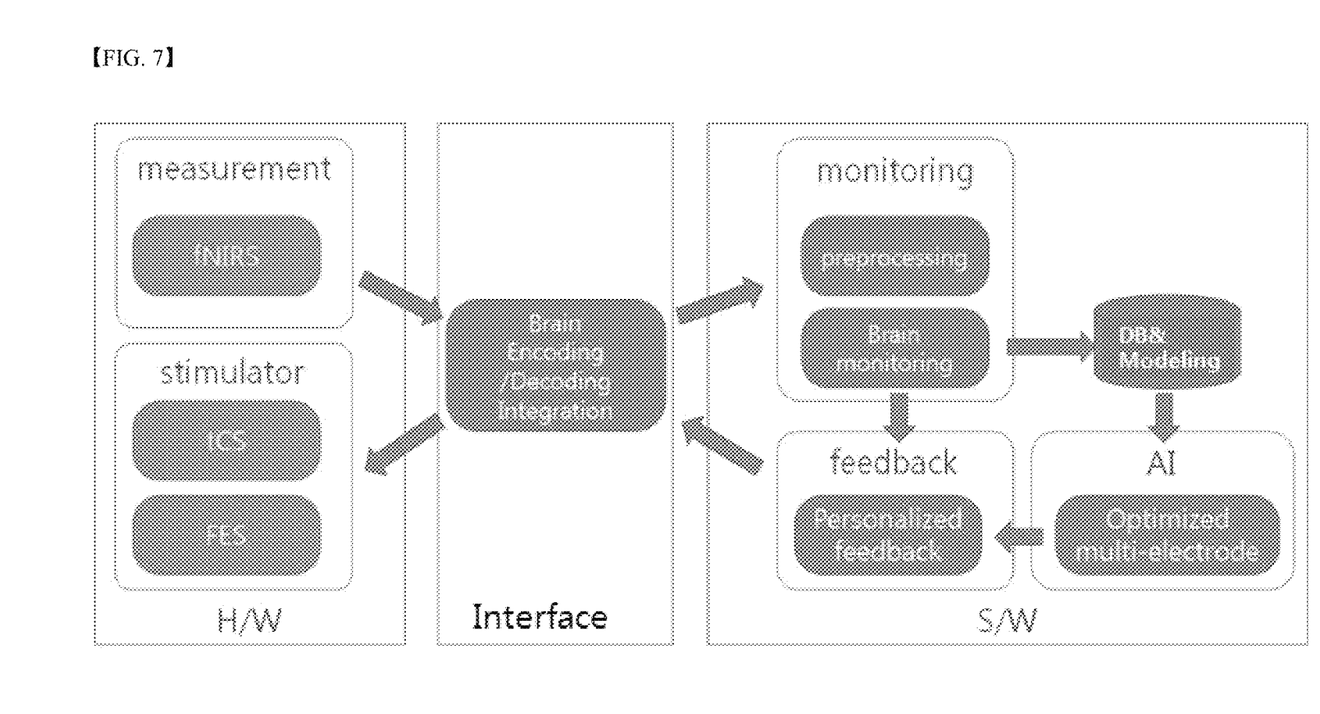
FIG. 7 is a view of a module device of a goggle connector for transcranial current stimulation and brain activity measurement according to the present invention.
Figure 8:
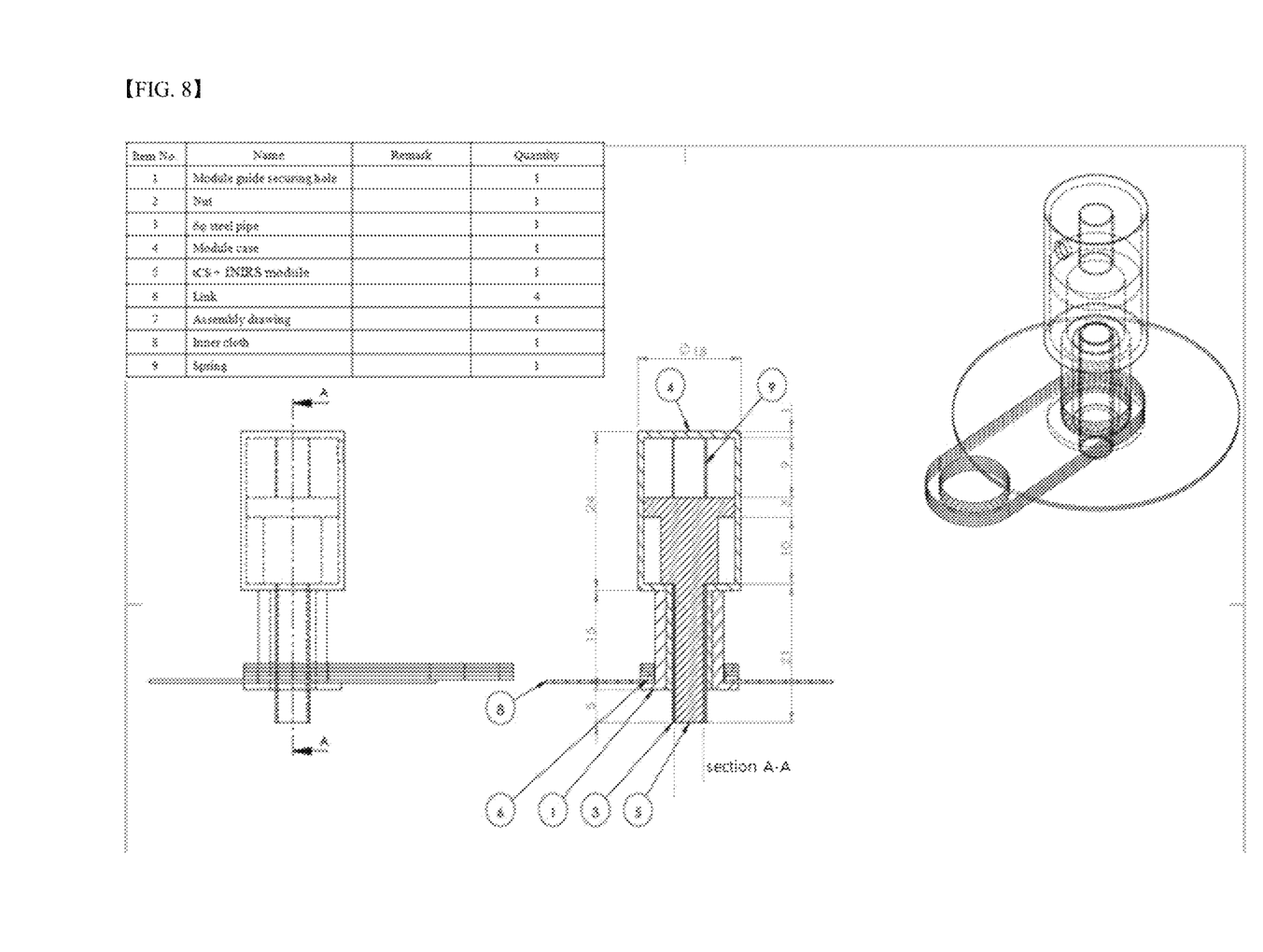
FIG. 8 is a sectional view and a perspective view of the goggle connector for transcranial current stimulation and brain activity measurement and the module device according to the present invention.
Figure 9:
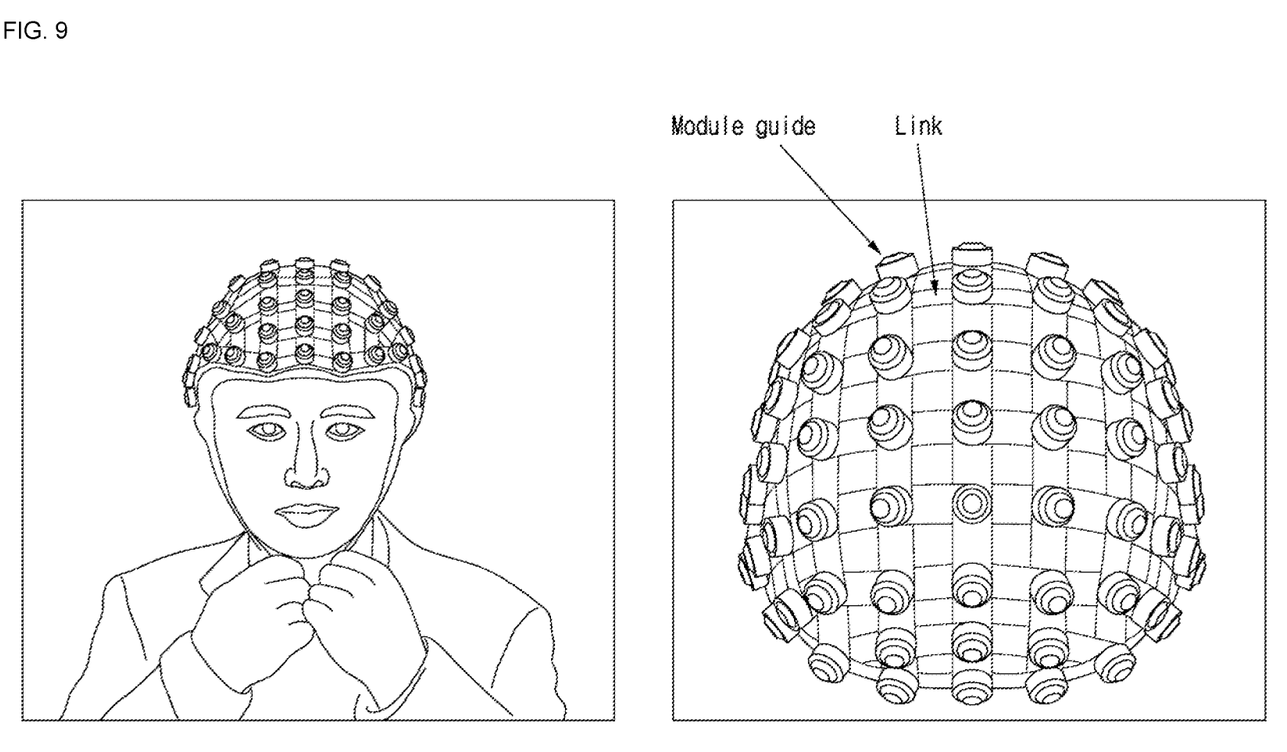
FIG. 9 is a picture showing a person wearing the goggles for transcranial current stimulation and brain activity measurement according to the present invention.

As shown in FIG. 7 and FIG. 8, the module guide includes: a module guide securing hole (①) formed in each of the punched portions of the goggles and having a cylindrical shape open at upper and lower sides thereof; a module case (④) inserted into the module guide securing hole (①) and having a cylindrical shape open at a lower side thereof and closed at an upper side thereof; a tCS+fNIRS module (⑤) disposed to move upwards or downwards in the module case (④) and having a lower end brought into contact with the scalp and composed of a piston-shaped steel pipe; and a spring (⑨) pushing an upper surface of the tCS+fNIRS module (⑤) in a downward direction in the module case (④).

The cranial nerve control device based on monitoring according to real-time brain activity change and combined central and peripheral nerve stimulation according to the present invention has effects in improvement in concentration, memory, exercise accuracy, language function, and swallowing function of normal adults and some stroke patients, and the like.

A brain activity measurement monitoring technique using functional near-infrared spectroscopy (fNIRS) is based on two major properties: first, the biological tissue allows light having a wavelength in the near infrared range to pass relatively well therethrough, and second, the tissue contains a small number of color-containing substances, i.e. chromophores, which exhibit variable light absorption depending on an oxidation state. The chromophores present in the brain tissue are oxyhemoglobin ($HbO_2$), deoxyhemoglobin (Hb), and oxidized cytochrome aa3 ($CytO_2$), which is present inside a cell mitochondria membrane and plays an important role in intracellular energy metabolism.

By observing a change in concentration of these chromophores through functional near-infrared spectroscopy (fNIRS), it is possible to measure not only the degree of oxygenation in the blood but also the degree of oxygenation in the cell, and to calculate cerebral blood flow, cerebral blood volume, and autoregulation of cerebral blood flow.

Further, functional electrical stimulation (FES) is defined as an act of creating functionally useful movement through application of electrical stimulation to a patient who has difficulty controlling movement due to damage to the upper motion neurons. In other words, the functional electrical stimulation (FES) is used for strengthening paralyzed muscles, improving the state of gait disorders, walking training, and assistive devices for patients having central nervous disorders, such as spinal cord injury, head trauma, stroke, and cerebral palsy.

The functional electrical stimulation (FES) is used to improve a hand gripping function or to prevent shoulder dislocation in patients with hemiplegia caused by stroke. Currently, in application of the FES to clinical practice, 40 Hz to 50 Hz is mainly used in the upper extremity muscle and 20 Hz to 30 Hz is used in the lower extremity muscle.

Chronic disorders in stroke patients are prominent in the distal part of the upper extremity. In particular, a finger stretching action is the most delayed recovery and requires active rehabilitation training, and a finger flexing action is a main target of the functional electrical stimulation.

Although some embodiments have been described herein, it should be understood that various modifications, variations, and alterations can be made by those skilled in the art without departing from the spirit and scope of the present invention. Therefore, the scope of the invention should be limited only by the appended claims and equivalents thereto.

INDUSTRIAL APPLICABILITY

According to the present invention, the cranial nerve control device based on monitoring according to real-time brain activity change and combined central and peripheral nerve stimulation can automatically control electrical stimulation through understanding of an activated state of the brain without targeting a damaged brain region, thereby providing convenience for enriched human life while enabling dramatic treatment of brain diseases, as a technology for automatically understanding functional activation of a user brain through real-time detection of structurally and functionally complex brain cognition based on artificial intelligence-based feedback of brain signals and brain electrical stimulation.

The invention claimed is:

1. A cranial nerve control device based on combined stimulation with respect to central and peripheral nerves, comprising:
   goggles worn on a patient's head to measure the patient's brain activity;
   a functional electric stimulator worn the patient's wrist to apply peripheral nerve stimulation to the patient;
   a plurality of module guides provided to the goggles and each of the plurality of module guides comprising a transcranial current stimulator-combined functional near-infrared spectroscopy measurement module which includes:
      a transcranial current stimulator adapted to apply central nerve stimulation to the patient; and
      a functional near-infrared spectroscopy measurement module adapted to measure the patient's brain activity in response to combined stimulation from the functional electric stimulator and the transcranial current stimulator;
   a functional electric stimulator controller adapted to control the functional electric stimulator;
   a transcranial current stimulator-combined near-infrared spectroscopy measurement module controller adapted to control the transcranial current stimulator-combined functional near-infrared spectroscopy measurement module; and
   a simulation device simultaneously connected to both the transcranial current stimulator-combined near-infrared spectroscopy measurement module controller and the functional electric stimulator controller to provide feedback of a transcranial current stimulation control signal to the transcranial current stimulator-combined near-infrared spectroscopy measurement module controller and feedback of a functional electrical stimulation control signal to the functional electric stimulator controller while monitoring the patient's brain activity, the transcranial current stimulation control signal, and the functional electrical stimulation control signal,
   wherein functional near-infrared spectroscopy-based hemodynamic monitoring software and a transcranial current stimulation interpretation program are installed in the simulation device to allow brain regions other than a damaged brain region of the patient to be stimulated through control of an electrode location and current intensity of the transcranial current stimulator while providing feedback thereof based on a brain activity state by functional electric stimulation and transcranial current stimulation,
   wherein each of the plurality of module guides further comprises a link for connection with another module guide.

2. The cranial nerve control device according to claim 1, wherein each of the module guides further comprises:
   a cylindrical member stood on each of a plurality of punched portions arranged on the goggles;
   a module case inserted into the cylindrical members and open at a lower side thereof and closed at an upper side thereof, the transcranial current stimulator-combined functional near-infrared spectroscopy measurement module being disposed inside the module case; and a spring disposed inside the module case and pushing an upper surface of the transcranial current stimulator-combined functional near-infrared spectroscopy measurement module in a downward direction.

3. The cranial nerve control device according to claim 2, wherein the transcranial current stimulator of the transcranial current stimulator-combined functional near-infrared spectroscopy measurement module comprises a steel pipe.

\* \* \* \* \*